United States Patent [19]

Watanabe

[11] Patent Number: 4,849,798
[45] Date of Patent: Jul. 18, 1989

[54] FIELD EFFECT TRANSISTOR TYPE SENSOR WITH AN AUXILIARY ELECTRODE

[75] Inventor: Masanori Watanabe, Nara, Japan

[73] Assignee: Sharp Kabushiki Kaisha, Osaka, Japan

[21] Appl. No.: 129,339

[22] Filed: Dec. 3, 1987

Related U.S. Application Data

[63] Continuation of Ser. No. 733,465, May 13, 1985, abandoned.

[30] Foreign Application Priority Data

May 16, 1984 [JP] Japan ................... 59-99320

[51] Int. Cl.[4] ............................... H01L 29/78
[52] U.S. Cl. ................... 357/23.15; 357/25; 357/23.14; 357/53; 357/51
[58] Field of Search .............. 357/23.15, 23.14, 23.1, 357/30, 51, 25, 53

[56] References Cited

U.S. PATENT DOCUMENTS

| | | | |
|---|---|---|---|
| 3,556,966 | 1/1971 | Waxman et al. | 357/23.15 X |
| 4,020,830 | 5/1977 | Johnson et al. | 357/25 X |
| 4,238,758 | 12/1980 | Suzuki | 357/23.15 X |
| 4,322,680 | 3/1982 | Janata et al. | 324/71 SN |
| 4,397,714 | 8/1983 | Janata et al. | 357/25 X |
| 4,411,741 | 10/1983 | Janata | 357/25 X |
| 4,446,474 | 5/1984 | Mizusaki et al. | 357/23.15 X |
| 4,489,340 | 12/1984 | Ueda et al. | 357/23.14 X |
| 4,514,263 | 4/1985 | Jawata | 357/25 X |
| 4,570,328 | 2/1986 | Price et al. | 357/23.15 X |

FOREIGN PATENT DOCUMENTS

| | | | |
|---|---|---|---|
| 3504401 | 8/1985 | Fed. Rep. of Germany. | |
| 53-10283 | 1/1978 | Japan | 357/23.15 |
| 1529743 | 10/1978 | United Kingdom | 357/23.15 |
| 2160708 | 12/1985 | United Kingdom. | |

Primary Examiner—Andrew J. James
Assistant Examiner—William A. Mintel
Attorney, Agent, or Firm—Spencer & Frank

[57] ABSTRACT

A field effect transistor-type sensor comprising a field effect transistor device incorporated with a sensitive means exhibiting electric variation due to a physical or chemical interaction with the physical quantity to be detected so that said sensitive means is disposed between a gate insulating film and a gate electrode of the transistor device, wherein an auxiliary electrode film for the application of a drift-cancellation voltage to said sensitive means is located between said gate insulating film and said sensitive means in such a manner that an extended portion of said auxiliary electrode film falls in a region over at least one part of a drain region of said transistor device.

10 Claims, 4 Drawing Sheets

FIG. 5
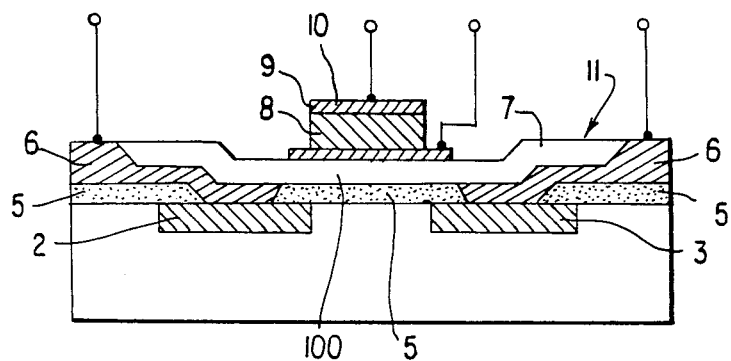
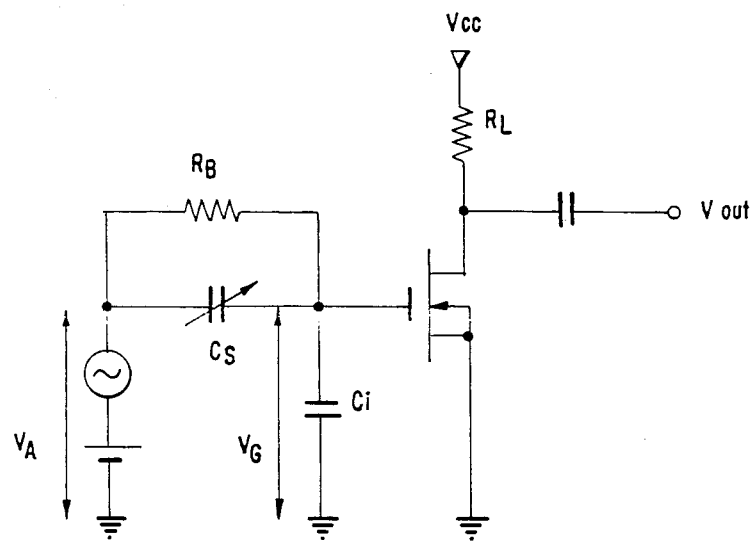
FIG. 6

FIELD EFFECT TRANSISTOR TYPE SENSOR WITH AN AUXILIARY ELECTRODE

This application is a continuation, of application Ser. No. 733,465, filed May 13th 1985, now abandoned.

BACKGROUND OF THE INVENTION

1. Field of the Invention

The present invention relates to a field effect transistor-type sensor for detecting a variation of the gate operation of a field effect transistor due to a variation of external factors, by a sensitive means formed on the gate insulating film of an MOS- or MIS-field effect transistor device.

2. Description of the Prior Art

A field effect transistor (hereinafter, referred to as FET)-type sensor, which comprises an FET device incorporated with a sensitive means exhibiting an electric variation of electrostatic capacity, electric conductivity, electrostatic potential, etc., due to a physical or chemical interaction with the physical quantity to be detected, detects the said physical quantity as a variation of the gate operation of the said FET device. Taking advantage of the high input impedance and the amplifying function of the FET device, such an FET type sensor can exhibit a high output, even though its size is extremely small, and thus is advantageous in actual use. Particularly an FET type sensor which is constructed in such a manner as to have a sensitive means on the gate insulating film of the FET device is advantageous practically and economically since the FET device can be small, and a number of devices can be formed on the same substrate. However, such an FET type sensor containing the FET device therein is inferior to an ordinary FET device alone in the operation stability of the FET device. It is also inferior to an FET device in the output stability and the reproducibility of the output characteristic. Depending upon the kind of the FET type sensor required, materials and production processes of the sensitive means are so different that the operation characteristic of the FET device can be remarkably varied. As compared with an ordinary FET device, a large amount of impurities and/or ions are apt to appear in the sensitive means or may contaminate the interface between the sensitive means and the gate insulating film during the formation of the sensitive means on the FET device, causing instability not only in the operation characteristic of the FET device but also in the output characteristic of the FET type sensor. Moreover, since the FET type sensor, which is designed to be used as an atmosphere sensor such as a gas sensor, a moisture sensor, etc., is exposed to an atmosphere, it will be contaminated by impurities in the atmosphere, causing variation and/or deterioration of the FET characteristic and/or deterioration of the sensor itself. Accordingly, an FET type sensor must be provided with an arrangement which will suppress the influence of impurities and/or ions contained in the materials of the sensitive means, or impurities and/or ions which contaminated the interface between the sensitive means and the gate insulating film during the formation of the sensitive means on the FET device and/or during operation of the FET device, thereby providing for a stable output characteristic over a long period of time. If such an FET type sensor is designed, a variety of sensors such as gas sensors, moisture sensors, ion sensors, biological sensors, infrared-ray sensors, etc., will be able to be produced in an FET type format. FET type gas sensors, moisture sensors, ion sensors and biological sensors cannot avoid direct interaction of the sensitive means with the atmosphere so that the device therein cannot be covered with a package, etc. Therefore, the above-mentioned problems deriving from the contamination, etc., of impurities and/or ions from the outside must be solved for FET type sensors. To solve these problems, a silicon nitride film having a small diffusion coefficient for ions, moisture, etc., has been used as the gate insulating film, or used to cover the surface of the FET device. The resulting FET sensors are, however, still inferior in output stability over a long period of time.

In order to solve the above-mentioned problems, the present applicant has proposed an FET type sensor having a double gate-electrode structure which was disclosed in U.S. patent application Ser. No. 697,640 and British Patent Application No. 8503061. This FET type sensor is excellent in output stability over a long period of time, but the following two problems still remain: One of them is that the characteristics of the FET device vary widely resulting in a wide variation of the sensor output. To correct this phenomenon, the selection of devices and/or the regulation of circuits is essential. The other is that the characteristics of the FET device depend upon temperature resulting in a variation of the output, and specific circuits are required to correct this phenomenon.

The following explanation of the operation of the above-mentioned FET type sensor proposed by the applicant makes possible a comprehensive understanding of these problems of the said FET type sensor:

As shown in FIG. 5, the FET type moisture sensor comprises an FET device 11 incorporated with a moisture sensitive means 9.

The FET device 11 is an MOS-type n-channel FET in which an n-type source 2 and an n-type drain 3 are formed in a row by the diffusion of phosphorus into the surface of a p-type silicon substrate 1. The surface of the silicon substrate 1 is covered by a silicon dioxide film 5 having through-holes for the source 2 and the drain 3. Double layers of the silicon dioxide film ($SiO_2$)5 and a silicon nitride film ($Si_3N_4$)7d disposed on the silicon substrate 1 form between the source 2 and the drain 3, a gate insulating film 100. The silicon nitride film 7 serving to protect the FET device 11 covers a portion of the upper face of each of the conductive electrode films 6, which are formed on the silicon substrate 1 and the silicon dioxide film 5, and which come into contact with the source 2 and their drain 3 at the ends, respectively, which extend through the holes in the film 5. On the gate insulating film 100, the moisture sensitive means 9 and a moisture permeable gate electrode film 10 are successively formed. A blocking film 8 made of a conductive film is located between the moisture sensitive means 9 and the silicon nitride film 7. The blocking film 8 serves as an auxiliary electrode which applies a drift-cancellation voltage to the moisture sensitive means 9.

FIG. 6 shows an equivalent network of the above-mentioned FET type moisture sensor, wherein references Cs and Ci are the electrostatic capacities of the moisture sensitive means 9 and the double layered gate insulating film 100, respectively; reference $R_L$ is a load resistor connected in series with the drain electrode 6; and reference $R_B$ is a resistor connected in series with the blocking film 8.

The basic operation of the FET type moisture sensor is explained as follows: In order to simplify the explanation, the case that the moisture sensitive means 9 is directly formed on the gate insulating film 100 without the blocking film 8, that is, the resistor $R_B$ is omitted in the equivalent network in FIG. 6, is described, first.

Given that the voltage to be applied to the moisture permeable gate electrode film 10 is $V_A$ and the threshold voltage of the FET device 11 is $V_{th}$, the drain current $I_D$ can be represented by the following equation (1):

$$I_D = \frac{\beta}{2}(V_A - V_{TH})^2, \beta = \frac{\mu n C W}{L} \qquad (1)$$

wherein $\mu n$ is a carrier mobility; L and W are the channel length and the channel width of the FET device, respectively; and C is an electrostatic capacity, in the case where an electrostatic capacity Ci of the gate insulating film is connected in series with an electrostatic capacity $C_s$ of the moisture sensitive means 9, and is represented by the equation (2):

$$C = \frac{C_s C_i}{C_s + C_i} \qquad (2)$$

Thus, given that the gate voltage $V_A$ is a constant value, moisture can be detected as a variation of the drain current $I_D$ with the variation of the electrostatic capacity $C_s$ of the moisture of the external atmosphere.

The role of the blocking film (i.e., auxiliary electrode film) 8 and the resistor $R_B$ in the operation of the moisture sensor is described below:

The blocking film 8 is connected with the moisture permeable gate electrode film 10 on the moisture sensitive means 9 by the resistor $R_B$ as shown in FIG. 6. A voltage $V_A$, which is composed of a DC voltage $V_A$ (DC) and an AC voltage of frequency f superposed thereon, is applied to the gate insulating film 100 and the moisture sensitive means 9 through the moisture permeable gate electrode film 10 and the blocking film 8 to thereby drive this FET type moisture sensor. In the case where the DC voltage $V_A$ (DC) is smaller than the withstand voltage of the gate insulating film 100 and a leakage current does not occur through the gate insulating film 100, the DC voltage component $V_G$(DC) of the effective gate voltage $V_G$ applied to the blocking film 8 becomes equal to the DC voltage $V_A$(DC), resulting in no DC potential difference between both surfaces of the moisture sensitive means 9. The DC voltage $V_A$ (DC) functions to give an optimum bias voltage in the $I_D$-$V_G$ characteristic of the FET device. In order that the FET type moisture sensor operates as a moisture sensor, that is, it detects the variation of the electrostatic capacity $C_s$ of the moisture sensitive means due to moisture in an atmosphere, the AC voltage $V_A$ (AC) is essential.

The AC voltage is described as follows:

In the case where the resistor $R_B$, having a resistance value which is sufficiently great as compared with the impedance $(2\pi f C_S)^{-1}$ of the moisture sensitive means 9 at frequency f, is connected to the blocking film 8 and the moisture permeable gate electrode film 10, resistance of $R_B$ is negligible and the AC voltage component $V_G$(AC) of the gate voltage $V_G$ can be represented by the equation (3):

$$V_G(AC) = \frac{C_s}{C_s + C_i} V_A(AC) \qquad (3)$$

This indicates that since $V_G$ (AC) varies with the values of the electrostatic capacity $C_s$ of the moisture sensitive means at the application of $V_A$ (AC) with a given amplitude, the output signal required for a moisture sensor can be detected as the AC amplitude of the drain current $I_D$. Thus, the modulation of an electric current flowing from the source 2 to the drain 3 while applying $V_A$ (AC) to the gate electrode film 10, can be detected by the conductive electrode film 6 as a detecting signal.

The output signal from the drain 3 can be represented by the equation (4):

$$V_{out}(AC) = -G_m R_L \frac{C_s}{C_s + C_i} V_A(AC) \qquad (4)$$

This indicates that the output signal depends upon the mutual conductance Gm of the FET device. It is well known that the Gm decreases with a rise in temperature and is different among FET devices.

Therefore, the FET type moisture sensor developed previously by the applicant has the problems that a wide variation of the characteristics among FET devices must be corrected by the regulation of circuits, and a wide variation of the output depending upon temperature must be corrected.

SUMMARY OF THE INVENTION

The FET type sensor of this invention which overcomes the above-discussed and numerous other disadvantages and deficiencies of the prior art, comprises a field effect transistor device incorporated with a sensitive means exhibiting electric variation due to a physical or chemical interaction with the physical quantity to be detected so that said sensitive means is disposed between a gate insulating film and a gate electrode of the transistor device, wherein an auxiliary electrode film for the application of a drift-cancellation voltage to said sensitive means is located between said gate isulating film and said sensitive means in such a manner that an extended portion of said auxiliary electrode film falls in a region over at least one part of a drain region of said transistor device.

A region located between said extended portion of the auxiliary electrode film and said drain region of the transistor device produces electrostatic capacity thereby attaining output stability.

The sensitive means is preferably a moisture sensitive means, the electrostatic capacity or the electric conductivity of which varies with the absorption and the desorption of water vapor or moisture. The moisture sensitive means is at least one selected from the group consisting of a cellulose derivative film, a vinyl derivative films, an organic or an inorganic solid electrolyte film or a metal oxide film.

Thus, the invention described herein makes possible the objects of (1) providing an FET type sensor which suppresses a wide variation of the characteristics of the FET device therein and/or drift of the output depending upon temperature, thereby maintaining a stable output characteristic over a long period of time; (2) providing an FET type sensor which produces electrostatic capacity in a region beween an auxiliary gate electrode and the drain region of the FET device, thereby attaining stable sensor operation; (3) providing an FET type sensor which can be produced at low cost using extremely simplified circuits; and (4) providing an FET type sensor which includes a moisture sensor for detecting moisture, a gas sensor for detecting gases, an ion sensor for detecting ions, an infrared ray sensor for detecting infrared rays, a pressure sensor for detecting pressures, a biological sensor for detecting organic substances, etc., which maintains stable operation and output characteristics over a long period of time and is easily reproducible.

BRIEF DESCRIPTION OF THE DRAWINGS

This invention may be better understood and its numerous objects and advantages will become apparent to those skilled in the art by reference to the accompanying drawings as follows:

FIG. 5 is a sectional front view showing an FET type moisture sensor previously proposed by the applicant.

FIG. 6 is an illustration of an equivalent network of the FET type moisture sensor shown in FIG. 5.

DESCRIPTION OF THE PREFERRED EMBODIMENTS

Figure 1:
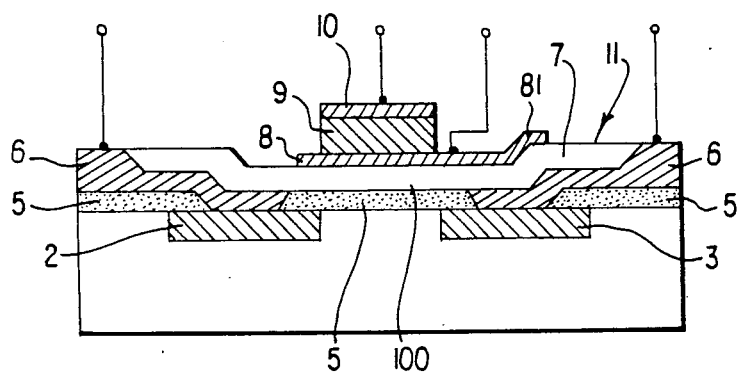
FIG. 1 is a sectional front view showing an FET type moisture sensor according to this invention.

FIG. 1 shows an FET type moisture sensor as an embodiment of the FET type sensor according to this invention, which comprises an FET device 11 incorporated with a moisture sensitive means 9.

The FET device 11 is a MOS-type n-channel FET in which an n-type source 2 and an n-type drain 3 are formed in a row by the diffusion of phosphorus the surface of a p-type silicon substrate 1. The surface of the silicon substrate 1 is covered by a silicon dioxide film 5 having through-holes for the source 2 and a drain 3. Double layers of the silicon dioxide film ($SiO_2$)5 and a silicon nitride film ($Si_3N_4$)7 disposed on the silicon substrate 1 form, between the source 2 and the drain 3, a gate insulating film 100. The silicon nitride film 7 serving to protect the FET device 11 covers a portion of the upper face of each of the conductive electrode films 6, which are formed on the silicon substrate 1 and the silicon dioxide film 5, and which come into contact with the source 2 and the drain 3 at their ends, respectively, which extend through the holes in the film 5. On the gate insulating film 100, the moisture sensitive means 9 and a moisture permeable gate electrode film 10 are successively formed, A blocking film 8 made of a conductive film is located between the moisture sensitive means 9 and the silicon nitride film 7. The feature of this invention is that an extended portion 81 of the blocking film 8 falls in a region over at least one part of the drain region 3 of the FET device 11 resulting in electrostatic capacity between the blocking film 8 and the drain region 3. The blocking film 8 serves as an auxiliary electrode which applies a drift-cancellation voltage to the moisture sensitive means 9.

The moisture sensitive means 9 is made of polyvinyl-alcohol or cellulose acetate crystallized by a baking treatment, but is not limited thereto. An organic or inorganic solid electrolyte film, a metal oxide film such as an aluminium oxide film, etc., can be used therefor. The moisture permeable gate electrode film 10 is made of a gold evaporation film having a thickness of about 100 Å, but it not limited thereto. The blocking film 8 is made of a gold or aluminum evaporation film having a thickness of about 2,000 Å, but is not limited thereto. The sensitive means 9 is not limited to a moisture sensitive means, but may be a gas sensitive means, an ion sensitive means, a chemical substance sensitive means, a heat sensitive means, a light sensitive means, etc. As the FET device, an MIS-type FET can be used.

The blocking film 8 is not required to be located between the silicon nitride film 7 and the moisture sensitive means 9. It can be located between, for example, the silicon dioxide film 5 and the silicon nitride film 7.

Figure 2:
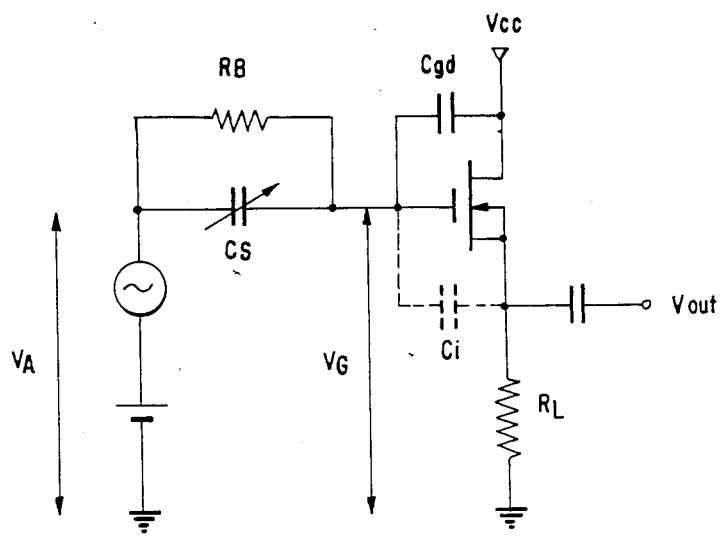
FIG. 2 is an illustration of an equivalent network of the FET type moisture sensor shown in FIG. 1.

FIG. 2 shows an equivalent network of the above-mentioned FET type moisture sensor, wherein references Cs and Ci are electrostatic capacities of the moisture sensitive means 9 and the double layered gate insulating film 100, respectively; reference $R_L$ is a load resistor connected in series with the drain electrode 6; reference $R_B$ is a resistor connected in series with the blocking film 8; and reference Cgd is an electrostatic capacity produced by the unique structure of the FET type sensor of this invention that the extended portion 81 of the blocking film 8 falls in a region over at least one part of the drain region 3.

The relationship between the AC voltage $V_G(AC)$ in the blocking film 8 and the output Vout (AC) can be represented by the equation (5):

$$Vout\ (AC) = \frac{GmR_L}{1 + GmR_L} V_G\ (AC) \tag{5}$$

wherein Gm is a mutual conductance of the FET device.

When the value of $GmR_L$ is sufficiently great, the Vout (AC) is substantially equal to the $V_G(AC)$ and independent of the Gm.

On the contrary, in the conventional sensor device shown in FIG. 5, the output Vout (AC) does not depend upon the capacity Cs of the sensitive film so that the device cannot operate as a sensor. This is because the equivalent network in FIG. 6 indicates that the capacity Ci of the gate insulating film decreases significantly. This can be explained by the equation (6):

$$V_G(AC) = \frac{Cs}{Cs + Ci(1 - Av)} V_A(AC) \tag{6}$$

wherein Av (represented by the equation:

$$Av = \frac{GmR_L}{1 + GmR_L}$$

is a voltage amplification coefficient of the FET device.

The equations (5) and (6) indicate that when the value of $GmR_L$ is sufficiently great to attain a stable output, the voltage amplification coefficient Av of the FET device becomes equal to approximately 1 and $V_G(AC)$ nearly equals $V_A(AC)$ without dependence upon the value of Cs. If the conventional FET type sensor is constructed such that the output can be independent of the mutual conductance Gm, the variation of the output signal is reduced therewith.

In order to solve the above-mentioned problem, the FET type sensor of this invention is designed in such a manner to produce electrostatic capacity $C_{gd}$ between the blocking film 8 and the drain region 3. The equation (6) is represented by the equation (7):

$$V_G(AC) = \frac{Cs}{Cs + C_{gd}} V_A(AC) \tag{7}$$

wherein the voltage amplification coefficient Av of the FET device is sufficiently great to become equal to 1. This is easily attained by the use of a constant-current circuit instead of the load resistor $R_L$ in the equivalent network shown in FIG. 2.

Equation (7) indicates that the FET type sensor of this invention operates as a sensor because the $V_G(AC)$, namely the Vout (AC), varied depending upon the electrostatic capacity Cs and that since the Vout (AC) becomes equal to the $V_G(AC)$, the output is independent of the variation of Gm and temperature.

To attain the optimum sensitivity of the FET type sensor, $C_{gd}$ must meet the following requirement: Given that the output at the time when the capacity Cs of the sensitive means 9 exhibits the minimum value Cs (min) is Vout (min) and the output at the time when the capacity Cs exhibits the maximum value Cs (max), $C_{gd}$ must be $\sqrt{Cs(min) \cdot Cs(max)}$ in order that the value of (Vout (max) - Vout (min)) exhibits the maximum value.

In order that the value of the Vout (max)/Vout (min) exhibits the maximum, $C_{gd}$ must be sufficiently greater than Cs.

Thus, the FET type sensor is preferably designed in such a manner that $C_{gd}$ equals or is greater than $\sqrt{Cs(min) \cdot Cs(max)}$ depending upon the characteristics of the sensitive means 9 and/or the necessity of signal treatments.

Figure 3:
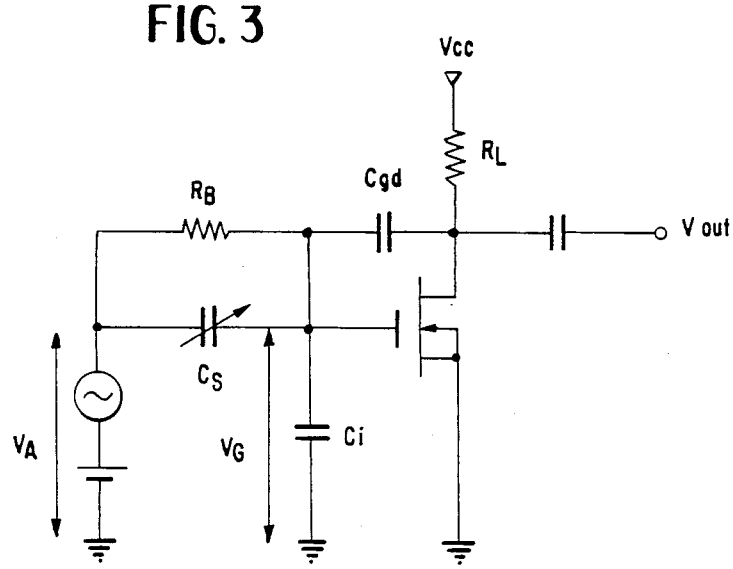
FIG. 3 is an illustration of another equivalent network of the FET type moisture sensor shown in FIG. 1.

FIG. 3 shows an equivalent network illustrating another operation of the FET type sensor of this invention. The output Vout can be represented by the equation (8):

$$Vout = \frac{Cs}{Cs + Ci + (1 + Av)C_{gd}} A'_V \cdot V_G(AC) \tag{8}$$

$$(A'_V = GmR_L)$$

In the case where the term $GmR_L$ is sufficiently great, Vout nearly equals $(C_s/C_{gd})V_G(AC)_L$ which is stabilized independently of the variation of Gm.

Figure 4:
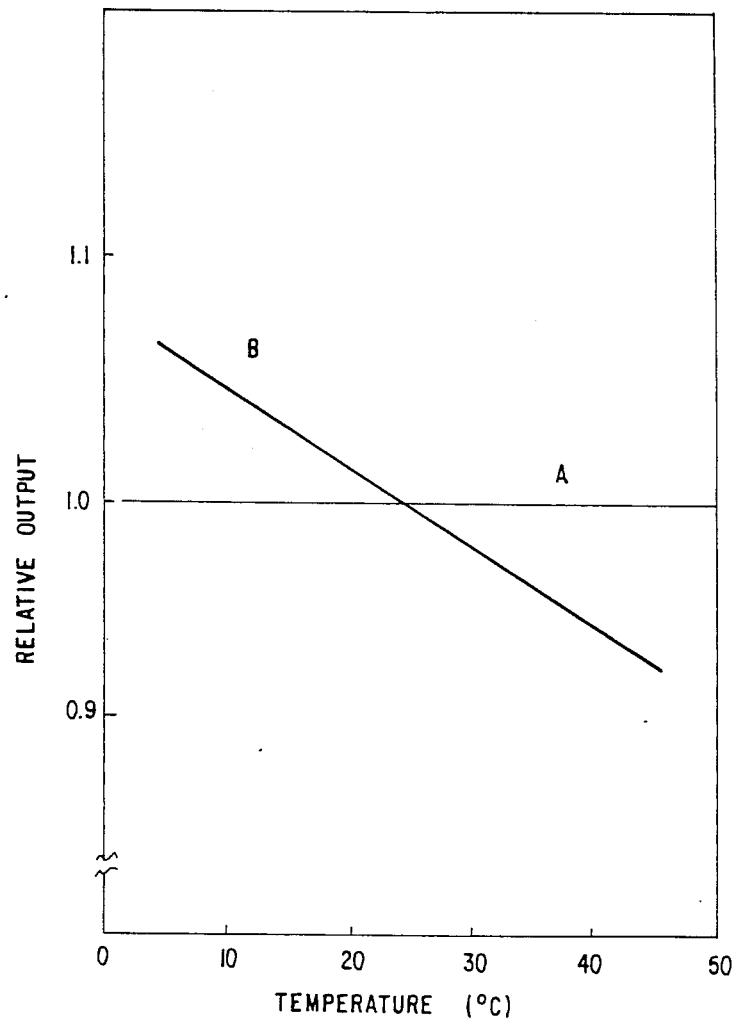
FIG. 4 shows characteristic curves, the curve (A) of which shows the dependence of the output on temperature in the equivalent network in FIG. 2 and the other (B) of which shows the dependence of the output on temperature in the equivalent network in FIG. 6.

FIG. 4 shows characteristic curves, a curve (A) of which shows the dependence of the output on temperature in the equivalent network shown in FIG. 2 with respect to the FET type sensor of this invention and the other (B) of which shows the dependence of the output on temperature in the equivalent network shown in FIG. 6 with respect to the conventional FET type sensor in FIG. 5, wherein the outputs were based on the experimental data at a relative humidity of 60% in the case that a baked cellulose acetate film was used as a moisture sensitive means 9 and the output in the curve A was determined by the use of a constant-current circuit of 100 μA instead of the load register $R_L$ in FIG. 2. FIG. 4 indicates that the FET type sensor of this invention can significantly suppress the dependence of the output on temperature.

It is understood that various other modifications will be apparent to and can be readily made by those skilled in the art without departing from the scope and spirit of this invention. Accordingly, it is not intended that the scope of the claims appended hereto be limited to the description as set forth herein, but rather that the claims be construed as encompassing all the features of patentable novelty which reside in the present invention, including all features which would be treated as equivalents thereof by those skilled in the art to which this invention pertains.

What is claimed is:

1. In a field effect transistor-type sensor of the type comprising: an MIS-field effect transistor device incorporated with a sensitive means for exhibiting electric variation due to a physical or chemical interaction with the physical quantity to be detected, said sensitive means being disposed between a gate insulating film and a gate electrode of said transistor device; means for applying a DC voltage having an AC voltage of a frequency f superimposed thereon to said gate electrode; and means for detecting the amplitude of the AC component of the drain current of said field effect transistor device as a measure of the variation of the impedance of said sensitive means; the improvement wherein an auxiliary electrode film for the application of a DC drift-cancellation bias voltage to said sensitive means during operation of said sensor is located between said gate insulating film and said sensitive means, said auxiliary electrode film having an extended portion which falls in a region over at least one part of a drain region of said transistor device such that the region located between said extended portion of said auxiliary electrode film and said drain region of said transistor device produces electrostatic capacity equal to or greater than $\sqrt{Cs(min) \cdot Cs(max)}$ for attaining output stability of said transistor device, wherein Cs(min) and Cs(max) are the minimum and maximum values of the electrostatic capacity of said sensitive means, respectively.

2. A field effect transistor-type sensor according to claim 1, wherein said sensitive means is a moisture sensitive means, the electrostatic capacity or the electric conductivity of which varies with the absorption and the desorption of water vapor or moisture.

3. A field effect transistor-type sensor according to claim 2, wherein said moisture sensitive means is at least one selected from the group consisting of a cellulose derivative film, a vinyl derivative film, an organic or an inorganic solid electrolyte film or a metal oxide film.

4. In a field effect transistor-type sensor comprising in combination: a semiconductor body having spaced source and drain regions formed therein adjacent one surface to define a channel region therebetween; an insulating layer covering said surface and having openings above said source and drain regions; source and drain electrodes contacting said source and drain regions, respectively, via the respective said openings; a sensitive dielectric film, which exhibits a variation of dielectric constant due to a physical or chemical interaction with a physical quantity to be detected, disposed on said insulating layer over said channel region; a gate electrode disposed on the outer surface of said sensitive dielectric film; means for applying a DC voltage having an AC voltage of a frequency f superposed thereon to said gate electrode; and means for detecting the amplitude of the AC component of the drain current of said field effect transistor-type sensor as a measure of the variation of the impedance of said sensitive dielectric film; the improvement comprising means, including an auxiliary electrode located between said insulating layer and said sensitive dielectric film, for applying a DC drift-cancellation bias voltage to said sensitive dielectric film, with said auxiliary electrode having an edge portion which extends laterally over said drain region to cause the region of said insulating layer between said portion of said auxiliary electrode and said drain region to produce electrostatic capacity equal to or greater than $\sqrt{Cs(min) \cdot Cs(max)}$ for attaining output stability of said transistor-type sensor, wherein Cs(min) and Cs(max) are the minimum and maximum values of the electrostatic capacity of said sensitive dielectric film, respectively.

5. A field effect transistor-type sensor as defined in claim 4 wherein: said source and drain electrodes extend laterally outwardly from said openings along the surface of said insulating layer; a further insulating layer completely covers the portions of said insulating layer not covered by said source and drain electrodes and at least a portion of said source and drain electrodes; said auxiliary electrode is disposed on the surface of said further insulating layer; and said portion of said auxiliary electrode extends over the surface of said further insulating layer to the region above said opening for said drain region.

6. A field effect transistor type sensor as defined in claim 5 wherein said semiconductor device is formed of silicon, said insulating layer is formed of silicon dioxide, and said further layer of insulating material is formed of silicon nitride.

7. A field effect transistor-type sensor as defined in claim 1 further comprising a resistor connected between said auxiliary electrode and said gate electrode of said transistor-type sensor, with the resistance value of said resistor being substantially greater than the AC impedance of said sensitive means at said frequency f of an AC voltage applied to said gate electrode.

8. A field effect transistor-type sensor as defined in claim 4 wherein: said means for applying a drift-cancellation bias voltage includes a resistance means connected between said gate electrode and said auxiliary electrode, with the resistance value of said resistance means being substantially greater than the AC impedance of said sensitive dielectric film at said frequency f of said AC voltage applied to said gate electrode.

9. A field effect transistor as defined in claim 8 wherein said resistance means is a fixed resistor.

10. A field effect transistor-type sensor as defined in claim 7 wherein: said sensitive means is a layer of insulating material which exhibits a variation in its dielectric constant due to a physical or chemical interaction with a quantity to be detected.

* * * * *

UNITED STATES PATENT AND TRADEMARK OFFICE
CERTIFICATE OF CORRECTION

PATENT NO. : 4,849,798
DATED : July 18th, 1989
INVENTOR(S) : Masanori Watanabe

It is certified that error appears in the above-identified patent and that said Letters Patent is hereby corrected as shown below:

On cover page below [57], after Abstract, last line, after "10 Claims," should read --3 Drawing Sheets--.

Signed and Sealed this

Twenty-third Day of October, 1990

Attest:

HARRY F. MANBECK, JR.

*Attesting Officer*     *Commissioner of Patents and Trademarks*